United States Patent [19]

Cartwright

[11] Patent Number: 4,840,664
[45] Date of Patent: Jun. 20, 1989

[54] HERBICIDAL PYRIDINE DERIVATIVES

[75] Inventor: David Cartwright, Reading, England

[73] Assignee: Imperial Chemical Industries PLC, London, England

[21] Appl. No.: 14,252

[22] Filed: Feb. 22, 1979

[30] Foreign Application Priority Data

Mar. 1, 1978 [GB] United Kingdom ............... 8127

[51] Int. Cl.$^4$ ................. A01N 43/40; C07D 213/64
[52] U.S. Cl. ............................. 71/94; 544/131; 546/194; 546/281; 546/300; 546/302
[58] Field of Search ............... 546/300, 302, 281, 194; 544/131; 71/94

[56] References Cited

U.S. PATENT DOCUMENTS

| 4,046,553 | 9/1977 | Takahashi et al. ............ 71/94 |
| 4,753,673 | 6/1988 | Johnston et al. ............. 71/94 |

FOREIGN PATENT DOCUMENTS

| 862325 | 6/1978 | Belgium . |
| 873844 | 5/1979 | Belgium . |
| 483 | 2/1979 | European Pat. Off. . |
| 1473 | 4/1979 | European Pat. Off. . |
| 2278675 | 2/1976 | France . |
| 2398059 | 2/1979 | France . |
| 52-54026 | 5/1977 | Japan ............................. 71/94 |
| 1507159 | 4/1978 | United Kingdom . |
| 1550574 | 8/1979 | United Kingdom . |

OTHER PUBLICATIONS

Dicks, J. et al., *Proceedings 1985 British Crop Protection Conference—Weeds*, 271–280.
Barrett, D., et al., *Proceedings 1985 British Crop Protection Conference—Weeds*, 231–238.
Karrer, P., *Organic Chemistry*, 2nd Edition, Elsevier Pub. Co., New York, 1946, pp. 92–102. QD 251 K32 1946.

*Primary Examiner*—Richard A. Schwartz
*Attorney, Agent, or Firm*—Cushman, Darby & Cushman

[57] ABSTRACT

Herbicidal pyridine compounds of formula (II):

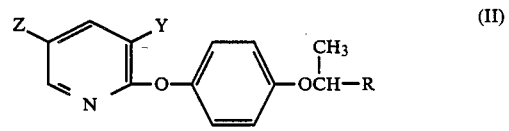

wherein Z is $CF_3$, $CF_2H$, $CF_2Cl$ or hydrogen; Y is hydrogen, Cl, or $CF_3$, provided that at least one of Y and Z is a halogenomethyl group; and R is a cyano group, or a carboxy group or a range of specified functional derivatives thereof; and wherein more than 50% by weight of the compound is in the D optical isomer form. The compounds are useful as selective herbicides for grass weeds in broad-leaved crops.

10 Claims, No Drawings

HERBICIDAL PYRIDINE DERIVATIVES

This invention relates to herbicidal pyridine compounds, to processes for preparing them, and to herbicidal processes and compositions utilising them.

In my U.S. application Ser. No. 29,341 I have described herbicidal pyridine compounds of the formula (I):

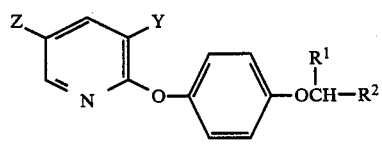

wherein Z and Y each represent a fluorine, chlorine, bromine, iodine, or hydrogen atom, or a trifluoromethyl, difluoromethyl, or chlorodifluoromethyl radical, provided that at least one of Z and Y is a halogenomethyl radical; $R^1$ represents hydrogen or an alkyl radical of 1 to 4 carbon atoms; and $R^2$ is a cyano group; a carboxyl group; a carboxamido group

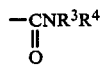

wherein $R^3$ is hydrogen or an alkyl radical and $R^4$ is hydrogen, an optionally hydroxy- or phenyl-substituted alkyl radical of 1 to 4 carbon atoms, a phenyl or chlorophenyl radical, an alkoxy radical of 1 to 4 carbon atoms, or a group $-NR^5R^6$ wherein $R^5$ is hydrogen or alkyl of 1 to 4 carbon atoms, and $R^6$ is hydrogen, alkyl of 1 to 4 carbon atoms, phenyl or chlorophenyl, or the group $-NR^3R^4$ constitutes a pyrrolidino, piperidino, or morpholino radical; a group

wherein $R^7$ is alkyl or phenyl; an alkoxycarbonyl group wherein the alkoxy group may be straight or branched, and which optionally bears one or more hydroxy, alkoxy, or halogen substituents, or bears a substituent of Formula (I) wherein $R^2$ represents a

radical; a group

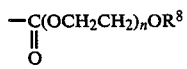

wherein $R^8$ is an alkyl radical of 1 to 4 carbon atoms and n is an integer from 1 to 5 inclusive; a cyclohexyloxycarbonyl radical optionally substituted by one or more halogen atoms or methyl radicals; an alkenyloxycarbonyl radical in which the alkenyl group contains from 3 to 6 carbon atoms; a phenoxycarbonyl radical optionally bearing one or more halogen or methyl substituents; or a benzyloxycarbonyl radical, the phenyl group of which optionally bears one or more halogen or methyl substituents; and, in the case of compounds wherein $R^2$ is a carboxyl group, salts thereof.

Preferred compounds of formula (I) include those wherein $R^1$ is a methyl group.

Particular examples of compounds of formula (I) include the compound in which Z is a $CF_3$ group, Y is hydrogen, $R^1$ is methyl, and $R^2$ is a butoxycarbonyl radical

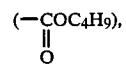

and the compound in which Z is a $CF_3$ group, Y is chlorine, $R^1$ is methyl, and $R^2$ is a propoxycarbonyl radical

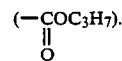

The compounds of the invention are herbicides which are in general substantially more effective against grass species than against broad-leaved species of plants. They may be used to control unwanted grass species growing alone, or at suitable rates of application they may be used to control grass weeds growing among broad-leaved crop plants. The compounds may be either applied to the soil before the emergence of the unwanted grass species (pre-emergence application) or to the above-ground parts of growing grass plants (post-emergence application).

The amount of the compound to be applied will depend upon a number of factors, for example the particular plant species whose growth is to be inhibited, but in general an amount of from 0.025 to 5 kilograms per hectare is usually suitable, and preferably from 0.1 to 1.0 kilograms per hectare.

The carbon atom adjacent to the carboxyl group in the above formula (I) is an asymmetric carbon atom. Accordingly, it is possible for the molecule to exist in two optical isomers. When prepared by chemical synthesis in the ordinary way, for example by the methods disclosed in Ser. No. 29,341, the compound (I) will be obtained as a racemic mixture of equal proportions of the D and L optical isomers.

It has now been discovered that the D optical isomer of compounds of the formula (I) possesses greater herbicidal activity than he L isomer. Mixtures of the D and L optical isomers of a particular compound (I) containing more than 50% by weight of the D isomer may therefore be expected to show greater herbicidal activity than the racemic mixtures of D and L optical isomers described in U.K. Patent Application No. 31321/78.

According to the present invention there are provided herbicidal pyridine compounds of formula (II)

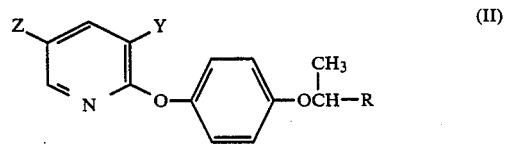

wherein Z is a trifluoromethyl, difluoromethyl, or chlorodifluoromethyl radical or hydrogen; Y is hydrogen, chlorine, or a trifluoromethyl radical, provided that at least one of Z and Y is a halogenomethyl radical, and R has the values defined for $R^2$ in relation to formula (I) above, and wherein more than 50% by weight of the compound is in the form of the D optical isomer.

Preferably at least 75% by weight of the compound is in the form of the D optical isomer, and more preferably at least 85%. Still more preferably, the proportion of the D isomer is at least 99%.

The D isomer of compounds of formula (II) may be obtained by stereospecific synthesis as shown in Scheme A below.

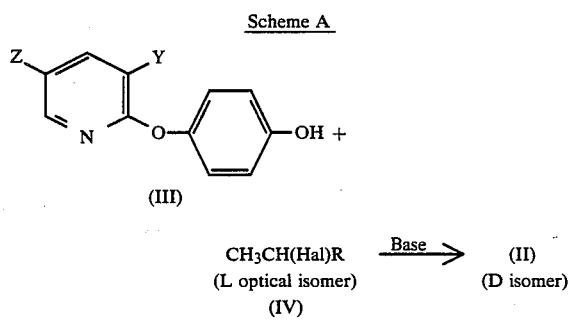

Scheme A

In Scheme A, the symbols Y, Z and R have the meanings defined for them in relation to formula (II) above. The symbol Hal stands for halogen, for example chlorine or bromine. During the reaction illustrated in Scheme A, the replacement of the bromine atom in the propionic acid derivative (IV) is accompanied by inversion of the optical configuration, giving rise to a product having the opposite optical configuration to that of the starting material. Thus to prepare compounds (II) in the D form, it is necessary to start with alpha-bromo propionic acid derivatives in the L form. The optical purity of the compound (II) prepared in this way will depend upon the optical purity of the alpha-halogeno propionic acid derivative used as starting material. Thus a starting material containing 90% of the L form of an alpha-bromo propionic acid derivative for example, will provide a product containing at the most 90% of the D form of the required product.

The starting material should preferably contain as near 100% of the L isomer of the alpha-halogeno propionic acid derivative as possible, so as to obtain a product which approaches as closely as possible to the herbicidal properties of the pure D isomer of compounds of formula (II). However, it may be convenient to use a starting material which contains somewhat less than 100% L isomer, although this will give rise to a product with less than the herbicidal effect of the pure D isomer of the particular compound II.

The reaction shown in Scheme A is preferably carried out in a solvent or diluent. Examples of solvents or diluents include ketones, for example methyl ethyl ketone, and aprotic solvents, for example dimethyl formamide, and dimethyl sulphoxide. The base may be for example an alkali metal carbonate, for example anhydrous sodium or potassium carbonate. The reaction may be accelerated by heating, for example to temperatures above 50° C., for example from 50° to 120° C.

A compound II having a particular value of R may be obtained directly by the process of Scheme A by choosing as a starting material the alpha-halogeno propionate (IV) with the appropriate R substituent. Alternatively, the R group in a compound prepared by the process of Scheme A may be converted by conventional chemical processes into the compound with the desired group R.

Thus, if desired, the process of Scheme A could be used to make a compound II in which R was a methoxycarbonyl group. This could then be hydrolysed by treatment with alkali by conventional methods to give the corresponding compound II in which R was a carboxyl group. This could than be converted to the corresponding acid chloride by treatment for example with thionyl chloride. The acid chloride so obtained (formula II, R=COCl) could be used to obtain a wide range of esters and amides by conventional processes.

The compounds III required as intermediates in Scheme A can be prepared by known methods, for example by the method used to make the known compound III in which Z and Y are both chlorine. This, compounds III may be prepared by reaction of a 2-halogeno-3,5-Y,Z-substituted pyridine with a metal salt of 4-methoxyphenol, so as to obtain a 2(4-methoxyphenoxy)-3,5-Y,Z-substituted pyridine, and then treating the latter with a dealkylating agent (e.g. pyridine hydrochloride) to generate the required compound III.

A further route for preparing the compounds of the invention is shown in Scheme B.

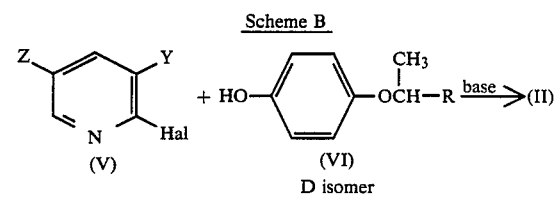

Scheme B

D isomer

In Scheme B, the symbols Y, Z and R have the meanings assigned to them above in relation to formula (II) and Hal is halogen, for example chlorine, bromine or fluorine. The starting materials (V) are known compounds or may be prepared by methods known for the preparation of analogous compounds; for example, the starting material (V) in which Z is $CF_2H$, Y is hydrogen and Hal is chlorine may be prepared by heating 2-chloro-5-formylpyridine with sulphur tetrafluoride in an autoclave at 150°–160° for 6 hours.

The compounds VI may be prepared by reaction of hydroquinone with the L optical isomer of the appropriate alpha-halogeno propionic acid derivative (IV), following methods known for the preparation of analogous compounds in racemic form.

The reaction conditions for the process of Scheme B are similar to those described for Scheme A.

In a further aspect, the invention provides a process of controlling graminaceous weeds, which comprises applying to the weeds or to the locus thereof a herbicidally effective amount of a compound of formula (II) as hereinbefore defined.

The invention further provides a process of selectively controlling graminaceous weeds in the presence of broad-leaved crops which comprises applying to the crop area a herbicidally effective amount of a compound of the formula (II) as hereinbefore defined.

The rate at which the compounds will be applied in the process of the invention will depend upon factors such as the identity of the particular graminaceous weeds and broad-leaved crop, but in general an amount of from 0.025 to 2.5 kilograms per hectare will be suitable, while from 0.1 to 1 kilogram per hectare is preferred.

In biological tests the D isomers were found to be significantly more active as herbicides than the L isomers when applied directly to plants. When applied to soil containing seeds of test plants, the D and L forms were similar in herbicidal activity which suggests that in soil the D and L isomers each racemise to give mixtures of the D and L forms.

In a further aspect, the invention provides herbicidal compositions, comprising as an active ingredient a compound of formula (II) as hereinbefore defined, in admixture with a carrier comprising a solid or liquid diluent.

Particular examples of compounds according to formula (II) above, containing more than 50% by weight of the D optical isomer are listed in Table I below:

TABLE I

| COMPOUND NO | Z | Y | R |
|---|---|---|---|
| 1 | $CF_3$ | H | $-COCH_3$ <br> $\parallel$ <br> $O$ |
| 2 | $CF_3$ | Cl | $-COCH_3$ <br> $\parallel$ <br> $O$ |
| 3 | $CHF_2$ | H | $-COC_4H_9$ <br> $\parallel$ <br> $O$ |
| 4 | $ClCF_2$ | H | $-COC_4H_9$ <br> $\parallel$ <br> $O$ |
| 5 | H | $CF_3$ | $-COC_4H_9$ <br> $\parallel$ <br> $O$ |

If desired, the compounds of formula (II) may be mixed with other herbicides.

Accordingly the invention further provides a herbicidal composition comprising a mixture of at least one herbicide of formula (II) above with at least one other herbicide.

The other herbicide may be any herbicide not having the formula (II). It may be a herbicide having a similar spectrum of herbicidal effect, that is to say a herbicide mainly effective against grasses, or it may be a herbicide having a complementary action, for example a herbicide that is active against broad-leaved weeds.

Examples of herbicides which may be mixed with the compounds of the invention include the following:
A. Bipyridylium herbicides, for example paraquat dichloride (1,1'-dimethyl-4,4'-bipyridylium dichloride) and diquat dibromide (1,1'-ethylene -2,2'-bipyridylium dibromide).
B. Glyphosate (N-phosphoromethylglycine) and its salts and esters.
C. Bentazon (3-isopropyl-(1H)-benzo-2,1,3-thiazine-4-one 2,2-dioxide).
D. Hormone herbicides
  e.g. MCPA (4-chloro-2-methylphenoxyacetic acid)
  2,4-D (2,4-dichlorophenoxyacetic acid)
  Dichlorprop (2-[2,4-dichlorophenoxy]propionic acid)
  2,4,5-T (2,4,5-trichlorophenoxyacetic acid)
  Mecoprop (2-[4-chloro-2-methylphenoxy]propionic acid).
E. Urea herbicides
  e.g. Chloroxuron (3-[4-(4-chlorophenoxy)phenyl]-1,1-dimethyl urea)
  Diuron (1-[3,4-dichlorophenyl]-3,3-dimethyl urea)
  Fluometuron (1-[metatrifluoromethylphenyl]-3,3-dimethyl urea).
F. Triazine herbicides
  e.g. simazine (2-chloro-4,6-diethylamino-1,3,5-triazine) atrazine (2-chloro-4-ethylamino-6-isopropylamino-1,3,5-triazine)
G. 1-alkoxy-1-alkyl-3-phenylurea herbicides
  e.g. linuron (3[3,4-dichlorophenyl /-1-methoxy-1-methyl urea)
  monolinuron (3-[4-chlorophenyl]-1-methoxy-1-methyl urea).
H. 1,2,4-Triazine-5-one herbicides
  e.g. metamitron (4-amino-4,5-dihydro-3-methyl-6-phenyl-1,2,4-triazin-5-one)
  metribuzin (4-amino-6-tertbutyl-4,5-dihydro-3-methylthio-1,2,4-triazin-5-one).
I. Anilide herbicides
  e.g. butachlor (N-butoxymethyl-α-chloro-2',6'-diethylacetanilide)
  alachlor (N-methoxymethyl-α-chloro-2',6'-diethylacetanilide)
  and propanil (3,4-dichloropropionanilide).
J. Haloalkanoic acids
  e.g. dalapon (2,2-dichloropropionic acid)
  TCA (trichloroacetic acid)
K. Diphenyl ether herbicides
  e.g. fluorodifen (4-nitrophenyl 2,-nitro-4,-trifluoromethylphenyl ether)
  2-nitro-5-(2-chloro-4-trifluoromethylphenoxy)benzoic acid
  and 2-chlorophenyl-3,-ethoxy-4,-nitro-4-trifluoromethylphenyl ether The mixtures of the invention generally contain from 0.1 to 10 parts, conveniently from 0.2 to 2 parts by weight of herbicide of formula (I) per part by weight of the other herbicide, depending upon the relative activity of the components. The amount of the mixture to be applied will depend upon a number of factors, for example the particular plant species to which the mixture is to be applied, but in general an amount of from 0.1 to 5.0 kilograms per hectare will usually be suitable.

The invention is illustrated by the following Examples, in which all parts are by weight and all temperatures are in degrees Centigrade unless otherwise specified.

EXAMPLE 1

This Example illustrates the preparation of the compound of formula (II) ($Z=CF_3$, $Y=H$, $R=-CO_2CH_3$) wherein 88% of the compound is in the D optical isomer form.

2-(4-Hydroxyphenoxy)-5-trifluoromethylpyridine (0.64 g) and methyl alpha-bromopropionate (0.42 g, L isomer content at least 88%), and anhydrous potassium carbonate (0.35 g) in methyl ethyl ketone (15 ml) were heated and stirred under reflux for 2 ½ hours. The mixture was cooled and filtered and the residue washed with methyl ethyl ketone. The filtrate and washings were evaporated to give an oil which was purified by chromatography on two silica gel plates (20×20 cm×2 mm thick) using a mixture of chloroform, petroleum ether (b.p. 60°–80° C.) and ethyl acetate in the proportions 75:25:5 by volume as the solvent.

The purified product was obtained as a colourless oil. Examination by nuclear magnetic resonance spectroscopy in the presence of an optical shift reagent showed the presence of 88% by weight of the D optical isomer. The optical rotations of this material at 20.5° $[\alpha]_D$ was measured in chloroform and found to be +27.8°.

Following the same procedure, but starting with the D isomer of methyl alpha-bromopropionate (at least 85% of the D isomer) the corresponding L isomer of the above compound was prepared for comparison purposes. Nuclear magnetic resonance spectroscopy with the aid of an optical shift reagent showed the presence of 85% by weight of the L isomer. The optical rotation at 21° $[\alpha]_D$ of this material in chloroform solution was $-29°$ ($\pm 2°$).

EXAMPLE 2

This Example illustrates the preparation of the compound of formula (II) (Z=CF$_3$, Y=Cl, R=—CO$_2$CH$_3$) wherein 89% of the compound is in the D optical isomer form.

3-Chloro-2-(4-hydroxyphenoxy)-5-trifluoromethylpyridine (0.75 g), methyl alpha-bromopropionate (0.42 g, L optical isomer content at least 89%), and anhydrous potassium carbonate (0.35 g) were stirred and heated under reflux in methyl ethyl ketone (15 ml) for 2½ hours. The mixture was cooled and filtered and the residue washed with methyl ethyl ketone. The filtrate and washings were evaporated to give an oil which was purified by thin-layer chromatography as described in Example 1, to give the product as a colourless oil (0.39 g).

This was found to contain 89% by weight of the D optical isomer, as measured by nuclear magnetic resonance spectroscopy with the aid of an optical shift reagent. The optical rotation at 20.5° $[\alpha]_D$ of this material in chloroform solution was found to be $+23.3°$ ($\pm 2°$).

Following the above procedure, but using the D optical isomer of methyl alpha-bromopropionate (at least 86% D isomer), the corresponding L isomer of the above compound was prepared for comparison purposes. The product contained 86% of the L optical isomer. The optical rotation at 21° $[\alpha]_D$ of this material was $-22.°$ ($\pm 3°$).

I claim:

1. A herbicidal pyridine compound of the formula (II)

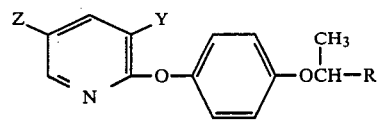

wherein Z is a trifluoromethyl, difluoromethyl, or chlorodifluoromethyl radical or hydrogen; Y is hydrogen, chlorine or a trifluoromethyl radical, provided that at least one of Z and Y is a halogenomethyl radical; and R is a carboxyl group; a lower alkoxycarbonyl group wherein the alkoxy group may be straight or branched, and which is unsubstituted or substituted with one or more hydroxy, alkoxy, or halogen substituents; or, in the case of compounds wherein R is a carboxyl group, a salt thereof; and wherein more than 50% by weight of the compound is in the form of the D optical isomer.

2. A herbicidal pyridine compound as claimed in claim 1 wherein at least 75% of the compound is in the form of the D optical isomer 3. A herbicidal pyridine compound as claimed in claim 1 wherein at least 85% of the compound is in the form of the D optical isomer.

4. A herbicidal pyridine compound as claimed in claim 1 wherein at least 99% of the compound is in the form of the D optical isomer.

5. A herbicidal pyridine compound as claimed in claim 1 wherein the group Z is CF$_3$, Y is hydrogen, and R is an alkoxycarbonyl group of 2 to 6 carbon atoms.

6. A compound as claimed in claim 5 wherein the group R is a butoxycarbonyl radical.

7. A compound as claimed in claim 1 wherein the group Z is CF$_3$, Y is chlorine, and R is an alkoxycarbonyl group of 2 to 6 carbon atoms.

8. A compound as claimed in claim 7 wherein the group R is a propoxycarbonyl radical.

9. A herbicidal composition comprising as an active ingredient an effective amount of a component of formula (II) as defined in claim 1 in admixture with a carrier comprising a solid or liquid diluent.

10. A method of controlling unwanted graminaceous weeds which comprises applying to said weeds a herbicidally effective amount of a compound according to claim 1 wherein more than 50% by weight of the compound is in the form of the D optical isomer.

* * * * *